United States Patent [19]

Bibb et al.

[11] 4,360,597

[45] Nov. 23, 1982

[54] STREPTOMYCES PLASMID AND CULTURE

[75] Inventors: Mervyn J. Bibb, Menlo Park, Calif.; David A. Hopwood, Norwich, England

[73] Assignee: National Research Development Corporation, London, England

[21] Appl. No.: 190,322

[22] PCT Filed: Jun. 1, 1979

[86] PCT No.: PCT/GB79/00095
§ 371 Date: Jan. 24, 1980
§ 102(e) Date: Jan. 24, 1980

[87] PCT Pub. No.: WO79/01169
PCT Pub. Date: Dec. 27, 1979

[30] Foreign Application Priority Data

Jun. 1, 1978 [GB] United Kingdom ............... 26219/78
Apr. 26, 1979 [GB] United Kingdom ................ 7914519
May 25, 1979 [GB] United Kingdom ................ 7918420

[51] Int. Cl.$^3$ ...................... C12N 1/20; C12N 15/00; C12N 1/00; C12N 1/02; C12Q 1/04
[52] U.S. Cl. .................................... 435/253; 435/172; 435/317; 435/261; 435/34
[58] Field of Search ......................... 435/172, 317, 253

[56] References Cited
PUBLICATIONS

Huber et al., Can. J. Microbiol., vol. 24, pp. 631 & 632, (1978).

Broda et al., Plasmids, pp. 4–11, W. H. Freeman and Co., Oxford and San Francisco, 1979.
Hopwood et al., "Genetic Recombination Through Protoplast Fusion in Streptomyces", Nature, 268, 171–174, (1977).
Hopwood, "Opening Address—The Many Faces of Recombination", Genetics of Industrial Microorganisms.
Bibb et al., "Transformation of Plasmid DNA Into Streptomyces at High Frequency", Nature, 274, 398–400, (1978).

Primary Examiner—Alvin E. Tanenholtz
Attorney, Agent, or Firm—Oblon, Fisher, Spivak, McClelland & Maier

[57] ABSTRACT

Novel Streptomyces plasmids have the characteristic that their presence in non-integrated form in a microorganism of the species Streptomyces lividans confers on that micro-organism the properties (a) of forming "pocks" when grown on a "lawn" of that strain of micro-organism deposited with the National Collection of Industrial Bacteria (NCIB) under the reference number 11416, and (b) of not forming "pocks" when grown on a "lawn" of that strain of micro-organism deposited with the NCIB under the reference number 11417, or which is derivable from a plasmid having such a characteristic by the removal or addition of DNA therefrom.

The plasmids are prepared from micro-organisms containing them or by the manipulation of other plasmids of the group and are of value as vectors for the introduction of nucleic acid into micro-organisms.

6 Claims, 1 Drawing Figure

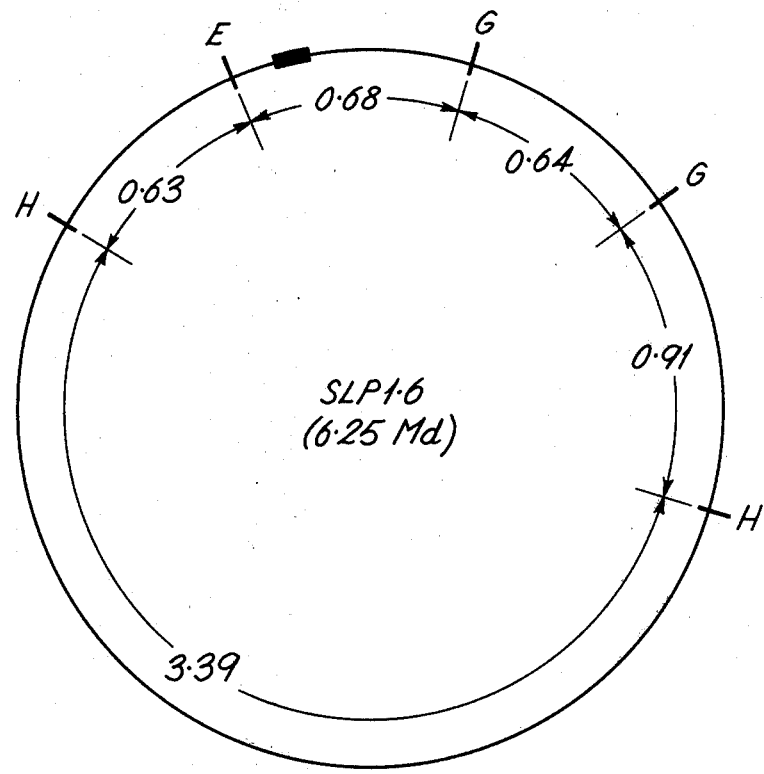

STREPTOMYCES PLASMID AND CULTURE

This invention relates to the incorporation of nucleic acid into cellular systems, to vectors for effecting such incorporation and to micro-organisms containing such vectors.

Methods for the incorporation of foreign nucleic acid into cellular systems have recently received much attention, the resultant modified cells being of interest either as a means of producing the foreign nucleic acid through replication of the cells or through the imparting of valuable properties to the cells by virtue of the presence of the foreign nucleic acid therein.

Much of the previous work in this area has involved the use of *Escherichia coli* as the host cellular system for the foreign nucleic acid but we have turned our attention instead to the genus Streptomyces and related genera, and have identified a novel group of plasmids of particular value as vectors for use with such micro-organisms.

Accordingly the present invention comprises a Streptomyces plasmid which has the characteristic that its presence in non-integrated form in a micro-organism of the species *Streptomyces lividans* confers on that micro-organism the properties (a) of forming "pocks" when grown on a "lawn" of that strain of micro-organism deposited with the National Collection of Industrial Bacteria (NCIB) under the reference number 11416, and (b) of not forming "pocks" when grown on a "lawn" of that strain of micro-organism deposited with the NCIB under the reference number 11417, or which is derivable from a plasmid having such a characteristic by the removal or addition of DNA therefrom.

Plasmids having the characteristic defined above constitute a related family isolable as covalently closed circular (ccc) DNA which possess a portion of their DNA sequence in common and thereby possess certain common properties throughout the family. The properties include the formation of "pocks" when a micro-organism of the species *S. lividans* containing a plasmid of this family in non-integrated form is grown on a "lawn" of the micro-organism NCIB 11416. The term "lawn" is employed herein, as in common usage, to indicate a confluent culture. The term "pocks" indicates foci of inhibition of growth of the cells constituting the lawn resulting from inhibition by the cells growing thereon; this phenomenon also being referred to as "tramlining" in relation to larger areas of inhibition. Such inhibition is believed to be analogous to the lethal zygosis described in the case of *E. coli*, being hereinafter referred to in this way, and is believed to result from a transfer of the plasmid into the cells forming the lawn from those growing on it.

The micro-organism NCIB 11416 is a strain of *S. lividans* which will function as a passive partner against which strains containing a non-integrated plasmid of this family will express lethal zygosis. This is believed to be because in NCIB 11416 a plasmid of this family capable of functional expression is absent although the strain is believed to contain such a plasmid in a form in which it is not expressible, presumably due to some type of integration. In contrast, the micro-organism NCIB 11417 is a strain of *S. lividans* which contains a plasmid of the family in non-integrated form and functionally expressible form. The presence of such a plasmid not only confers resistance against lethal zygosis initiated by a strain of *S. lividans* containing that plasmid but it has also been found that the inter-relation between plasmids of this family is such that lethal zygosis does not occur when a strain of *S. lividans* containing a plasmid of the family is grown on a lawn of a strain containing that plasmid or any other plasmid of the family in functionally expressible form.

It will be appreciated that the present invention extends to plasmids as defined above in isolated form, i.e. when not present in a micro-organism, or when present in a micro-organism. The invention thus includes a micro-organism containing such a plasmid. Also included by the invention is a culture system comprising a micro-organism containing a plasmid as defined herein together with a culture medium therefor. Such a medium will generally be a synthetic or artificial one although certain of the ingredients incorporated therein may of course be of natural occurrence. Various media described in the art for the culture of Streptomyces are suitable but among these R2 medium is of particular interest. The micro-organism will most usually be a strain of *Streptomyces lividans* but may also be a Streptomyces of another species particularly since the plasmids may be transferable from an *S. lividans* strain to a strain of another species by crossing as described hereinafter. Micro-organisms of particular interest are those in which the plasmid is present in functionally expressible form in terms of the exhibition or not of lethal zygosis in relation to two appropriately selected strains of the same species, and accordingly the present invention especially includes a micro-organism of the species *Streptomyces lividans* characterised by the properties (a) of forming "pocks" when grown on that strain of micro-organism deposited with the NCIB under reference number 11416, and (b) of not forming "pocks" when grown on that strain of micro-organism deposited with the NCIB under the reference number 11417.

Furthermore, the invention especially includes a Streptomyces plasmid whenever isolated from such a micro-organism as just defined. However, it has been found that the plasmid may readily be isolated from only a proportion of those micro-organisms fulfilling the functional tests for the presence of a plasmid. Isolation is conveniently effected, and the ability of a micro-organism to yield the plasmid is conveniently tested for, by lysis of the cells of the organism, for example using an enzyme such as lysozyme and a surface active agent such as sodium dodecyl sulphate (SDS), followed by separation of the DNA constituting the plasmid from chromosomal DNA, for example by caesium chloride centrifugation in the presence of ethidium bromide.

A group of micro-organisms exemplifying a range of plasmids according to the present invention has been deposited with the NCIB on May 25, 1978 in respect of NCIB 11417 (and also 11414, 11415 and 11416 which are referred to herein), on Apr. 19, 1979 in respect of 11499 and 11500, and on May 24, 1979, in respect of 11501, 11502 and 11503.[1] The NCIB reference numbers accorded to these micro-organisms are indicated in Table 1 given below, together with the corresponding John Innes reference numbers for these micro-organisms and the plasmids isolable therefrom. Such micro-organisms, and other micro-organisms of this invention, are of special interest when in a biologically purified form, i.e. free from at least a proportion of other strains of micro-organism with which they are in admixture in their original occurrence (natural or otherwise). The micro-organisms are preferably in biologically pure form, i.e. essentially free from other strains of microorganism, particularly of other Streptomyces. However, on storage, a proportion of the cells of strains containing a plasmid may spontaneously lose the plasmid so that they are then present in admixture with a proportion of strains not containing the non-integrated plasmid. The biological purity of such micro-organisms is then qualified by the presence of such "revertant" micro-organisms. It is of course possible, if desired, to repurify the original strain after such "reversion".

[1]Certain of these NCIB deposits have been duplicated by deposits made with the Deutsche Samlung von Mikro-organismen (DSM) on May 28, 1979.DSM 1567 corresponds to NCIB 11416 and other correspondence as shown in Table 1.

TABLE 1

| Strain of S. lividans | | | Plasmid contained |
|---|---|---|---|
| Reference number NCIB | John Innes | DSM | John Innes Reference number |
| 11417 | M170 | 1568 | SLP1.1[i] |
| 11499 | M180 | 1569 | SLP1.2 |
| 11500 | M183 | 1570 | SLP1.3 |
| 11501 | M221 | 1571 | SLP1.4 |
| 11502 | M222 | 1572 | SLP1.5 |
| 11503 | M223 | 1573 | SLP1.6 |

[i]Designated SLP1 in U.K. Patent Application No. 26219/78.

The micro-organism deposited under the NCIB reference number 11416 (John Innes Institute reference number 1326) referred to above has the same taxonomy as the wild type strain which is described in the article by Krasilnikov et al, The Biology of Certain Groups of Actinomycetes (editor Krasilnikov), published by Science Press, Moscow, 1965, 74, at pages 109 and 110 thereof and, indeed, is believed to be the strain originally isolated by Krasilnikov. The micro-organisms deposited under the NCIB reference numbers 11417, 11499, 11500, 11501, 11502 and 11503 again have the same taxonomy as the wild type strain but differ from it in that each contains an autonomous plasmid separate from the chromosome. The present invention particularly includes these specific micro-organisms and the plasmids isolable therefrom.

The derivation of these micro-organisms is as follows. The micro-organisms NCIB 11417, 11499 and 11500 were obtained by the culture of certain of the strains constituting the pocks arising on culture of the micro-organism NCIB 11416 on plates of R2 medium. Such pocks arise from the presence of a very low level of occurrence of variant strains among the micro-organisms constituting the type strain NCIB 11416. The micro-organisms NCIB 11501, 11502 and 11503 were obtained by means of a generally applicable procedure which comprises crossing a S. lividans micro-organism containing a non-integrated plasmid of this family with another species of Streptomyces such as S. coelicolor or S. parvulus and then crossing the resulting Streptomyces of the other species with another S. lividans micro-organism such as NCIB 11416. It is not clear, however, whether such crossing procedures give rise directly to the strains containing the new plasmids of the family or whether the presence of these plasmids in the S. lividans strains used in the crosses merely becomes apparent during the manipulations used in the crossing procedures. The specific procedures used for these three micro-organisms were as follows. A cross of the S. lividans strain NCIB 11499 with the S. coelicolor strain NCIB 11414 gave the S. coelicolor strain of John Innes reference number M200 and this was followed by a further cross of M200 with S. lividans NCIB 11416 which gave a group of strains, two of which were NCIB 11502 and 11503. A second, similar procedure involved a cross of the S. lividans strain NCIB 11417 with the S. coelicolor strain 11414 to give the S. coelicolor strain of John Innes reference number M171 followed by a further cross of M171 with S. lividans NCIB 11416 to give a group of strains, one of which was NCIB 11501. S. coelicolor strains M200 and M171 were selected by their ability to show lethal zygosis against a lawn of the passive S. coelicolor strain 11414, the phenomenon being a general one among strains of the same species of Streptomyces for other species as well as lividans. As indicated above, the crossing procedures specifically described may be varied both with regard to the S. lividans strains used, substituting another S. lividans strain such as one of strains NCIB 11500, 11501, 11502 and 11503 for NCIB 11499 or NCIB 11417 or another S. lividans strain not expressing the plasmid for NCIB 11416, and to the S. coelicolor strains used, substituting another S. coelicolor strain such as the strain NCIB 11415 for NCIB 11414 or substituting a strain of a third Streptomyces species such as S. parvulus for NCIB 11414.

The six plasmids SLP1.1 to SLP1.6, which are sex factors, each appear to be self-replicating and self-transmissible, and have been found to be of varying size ranging from an estimated 6.25 megadaltons for SLP1.6 to an estimated 8.23 megadaltons for SLP1.2, and to contain varying numbers of sites for cleavage by various restriction endonucleases. The structure of the plasmids is described in more detail in Example 1 at page 18 to 19 and is summarised in Table 2 thereof. It is believed that the presence of non-integrated plasmids of this family such as SLP1.1 to SLP1.6 in micro-organisms such as NCIB 11417 and 11499 to 11503 arises through the splitting out or copying of part of the sequence of integrated nucleic acid in the micro-organism (although it is believed that chromosomally integrated plasmid also is present in strains such as these). Moreover, it is believed that the portion of DNA thereby transferred from integrated to non-integrated form is variable, containing a common portion which dictates the properties of the plasmid as defined hereinbefore together with a variable portion of the chromosomal DNA. Such a hypothesis explains the varying size of the plasmids SLP1.1 to SLP1.6 and the existence therein of a common portion of DNA as indicated in Table 2.

It will be appreciated that in addition to variations in the plasmids of the family described herein which are believed arise from the operation of the phenomenon described above in their in vivo generation, it is also possible to manipulate a plasmid in vitro to produce another member of the family by techniques such as cleavage with a restriction endonuclease followed by ligation which are described hereinafter in more detail in relation to the use of the plasmids as vectors. By such techniques one may remove portions of the DNA constituting the plasmid which are not vital to the functional expression of lethal zygosis as described hereinbefore. On the basis of the hypothesis advanced above, such DNA clearly includes chromosomal DNA but may also include certain portions of the DNA common to all plasmids generated without any in vitro involvement in their history, since not all of this may be necessary to the expression of lethal zygosis. Plasmids of the family may also be produced by the incorporation of extra DNA through in vitro manipulation as defined hereinafter.

In summary, therefore, plasmids according to the present invention may be obtained by various means, including directly from naturally occurring micro-organisms, from micro-organisms obtained by manipulation of such naturally occurring micro-organisms, and by the in vitro manipulation of plasmids obtained from either of such sources. Accordingly, it will be appreciated that the term "Streptomyces plasmid" as used herein does not imply any limitation that the plasmid is obtained directly from a Streptomyces micro-organism containing it.

The identity of such plasmids produced by in vitro manipulation, or indeed of any plasmid, as being one of the family according to the present invention may be ascertained through the transformation into the strain of micro-organism deposited with the NCIB under reference number 11416, using techniques described hereinafter, and the subsequent study of the properties of the new strain thereby produced with respect to pock formation on NCIB 11416 and NCIB 11417. The transformed NCIB 11416 strain will, as an alternative criterion if required, no longer act as passive partner against which a strain such as NCIB 11417 shows lethal zygosis. The procedures involved in pock detection are specifically exemplified in Example 2. In general, cells of the strain to be tested for active expression of lethal zygosis are cultured on a suitable medium, for example R2 medium, together with cells of the strain which is the passive partner, the latter being at a sufficient density to provide a confluent lawn. After a suitable period of growth, usually from 2 to 7 days, for example 3 days, pock formation against the lawn will occur in appropriate instances. In the event that pocks do not appear, growth is conveniently continued until the lawn sporulates, the occurrence of sporulation without pock formation providing a sufficient indication of the absence of the lethal zygosis phenomenon.

Furthemore, it will be appreciated that although the lethal zygosis phenomenon provides a ready method of identifying a plasmid according to the family covered by the present invention, it is nevertheless possible that valuable plasmids may be produced by the removal of such a portion of their DNA content that the plasmid no longer expresses the lethal zygosis phenomenon but retains the ability to replicate, or even that the addition of DNA could have such an effect under certain circumstances. Accordingly the present invention includes such derived plasmids which do nevertheless contain a portion of their DNA sequence in common with other members of the group, and which may alternatively be defined as constituting plasmids which comprise that portion of the DNA sequence of the plasmid referred to herein as SLP1.6, this being the plasmid which is obtainable from the micro-organism deposited with the NCIB under No. 11503, which is required for replication. It will be appreciated from the foregoing discussion that such a plasmid may be larger or smaller than SLP1.6 and may be in isolated form or in a micro-organism, particularly a strain of S. lividans, especially in non-integrated form.

The presence of cleavage sites for various restriction enzymes in plasmids according to the present invention such as SLP1.1 to SLP1.6 renders the plasmids of particular interest as vectors for nucleic acid, particularly DNA, inserted at such a site or sites in the plasmid. Of especial interest in this respect are plasmids containing a single cleavage site for one particular enzyme, so that SLP1.1 and SLP1.5 are of interest as possessing a single site for SalPI (≡PstI) whilst SLP1.2 is of interest as possessing a single site for BamHI. The particular value of these sites, as compared with the single site for EcoRI in all of the plasmids, is that they occur in the extra segment of these plasmids not present in SLP1.6 and accordingly the insertion of DNA therein should not damage functions essential for plasmid replication.

The insertion of foreign or additional DNA into the plasmids may be effected, for example, by using recent developments in recombinant DNA technology such as those described by Collins, Current Topics in Microbiology and Immunology, 1977, 78, 121 and also described in other areas of the quite broad area of art now existing in relation to these techniques. The method used, which is exemplified hereinafter in the Examples, conveniently comprises digesting the plasmid with an appropriate restriction endonuclease to effect cleavage at a target site therein. Digestion may be effected at one site only in which case the DNA of the original plasmid is retained in the final plasmid incorporating the additional DNA or at more than one site in appropriate circumstances since it may be possible to discard certain of the orginal portion of the plasmid DNA whilst still retaining appropriate properties in the final plasmid constituted of part of the original DNA together with the foreign DNA. Following digestion, the cleaved plasmid DNA is conveniently joined to the additional DNA by ligation, for example using a DNA ligase, the additional DNA conveniently having been tailored to have suitable ends for ligation to the cleaved ends of the plasmid. Isolation of the reconstituted plasmid is then conveniently effected by screening for clones which can be identified as containing this reconstituted plasmid, for example by a fractionation procedure based on size and/or through the identification of an inherent property in the plasmid or more conveniently of a marker introduced therein through the additional DNA such as resistance to a particular antibiotic. As an alternative, a crude or at least a partially purified mixture of original and reconstituted plasmids may be used in the next stage.

As indicated above, the plasmids of the present invention provide a very suitable means for introducing additional DNA into a micro-organism. More usually, such additional DNA will include DNA introduced into the plasmid by the in vitro manipulation thereof, although plasmids isolated from natural sources may also be introduced without further manipulation if so required. Usually, however, the DNA introduced will be at least in part foreign to the host micro-organism. Although incorporation into micro-organisms of other genera, for example related Actinomycetes such as *Streptosporangium,Actinoplanes*, and especially Nocardia and Micromonospora may be considered, the main area of interest lies with the Streptomyces. Conveniently, such incorporation is effected by the use of a suitable transformation method although other procedures such as transduction and conjugation may be used. Incorporation by such procedures is well described in the art. Among the various methods available for effecting transformation which are described in the art, one is of particular interest. This method comprises the uptake of the DNA, which is generally in covalently closed circular form, by protoplasts obtained from the host micro-organism, various methods described in the art being suitable for the production of such protoplasts, for example the use of lysozyme, particularly following treatment with glycine. Among methods for inducing protoplasts to take up DNA we have found that the use of polyethylene glycol (PEG) gives particularly good results. A preferred concentration range of PEG in the medium used is from 5 or 10 to 50 or 70% w/v, particularly from 10 to 30% w/v, for example 20% w/v. Following incubation of the protoplasts with the DNA the protoplasts are cultured on a suitable regeneration medium for cell wall formation and growth, such as R2 medium, conveniently using serial dilution in application to the medium.

Following transformation, or other procedure for incorporating the plasmid, it is of course necessary to detect and isolate microorganisms which result from its incorporation. A particularly suitable procedure for doing this relies upon the phenomenon of lethal zygosis and corresponds essentially to the first functional test for identifying a plasmid of the family according to this invention as described above, i.e. the formation of pocks on NCIB 11416. The cells obtained at the end of the incorporation procedure, for example on the regeneration of protoplasts, may represent mixtures or single colonies depending on the dilution level, etc. One of two procedures is therefore usually employed. Thus, either a mixture of cells is used in the assay procedure in serial dilutions, or samples of single colonies are used. In either case the identification of a colony of a micro-organism incorporating a plasmid of the family is made by the occurrence of pocks. Where such a colony is applied singly in the first instance, the original colony may then be cultured further to produce the micro-organism in quantity, but where the colony is derived from a mixture, then a sample may be removed from the centre of the "pock" on the lawn and cultured to produce quantities of the micro-organism. The latter procedure is that which is more generally used in cloning procedures.

The incorporation of plasmids according to the invention which are capable of replication but not of exhibiting lethal zygosis is of course not amenable to detection in this particularly convenient manner and such a procedure is of course also only applicable where the original micro-organism does not contain a plasmid according to the invention which itself produces lethal zygosis against a lawn of NCIB 11416. It will be appreciated that the present invention particularly includes micro-organisms containing a plasmid as defined herein when incorporated therein by manipulative procedures as described above and particularly by transformation.

Although the plasmids can be used as vectors for various forms of foreign DNA and for the purpose of producing quantities of the DNA by cultivation of the micro-organism into which it has been introduced, the area of particular interest involves the production of antibiotics. Various species of Streptomyces can produce antibiotics in culture, including *S. coelicolor, S. rimosus, S. venezuelae* and *S. clavuligerus*, and DNA may be transferred between certain different strains or species using the plasmids according to the present invention with the broad aim of strain improvement, particularly the improvement of characteristics of the micro-organism which are relevant to industrial fermentation, for example the production of new antibiotics, increased yields of antibiotics, improved fermentation characteristics etc. Specifically, such procedures include the introduction of genes coding for various potential antibiotic side-chains or for the addition or removal of functional groups on the molecules, as well as the introduction of genes coding for appropriate hydrolytic enzymes to allow the culture to be grown on cheaper carbohydrate sources or the amplification of gene products involved in rate-limiting biosynthetic steps.

The invention is illustrated by the following Examples.

EXAMPLE 1: PREPARATION OF PLASMID

The preparation from a micro-organism of a plasmid of the present invention is divided into the steps of identifying and isolating a micro-organism containing such a plasmid and then isolating the plasmid from the micro-organism. A generally applicable description is given in relation to both steps with particular reference to strains which have been subjected to these general procedures and to specific micro-organisms and plasmids isolated thereby.

ISOLATION OF MICRO-ORGANISM

(A) Direct Procedure

Spores of the *S. lividans* strain NCIB 11416 are spread on plates of R2 medium (Hopwood and Wright, Molecular and General Genetics, 1978, 162, 307) and grown thereon, when some pocks are observed. Using a fine needle, growth is picked from the centre of a pock and streaked out on a plate of the minimal medium described by Hopwood in Bacteriological Reviews, 1967, 31, 373 (MM) to give single isolated colonies. These are grown up and then replica plated using a velvet pad on to a plate of R2 medium spread with a lawn of spores of the strain NCIB 11416. Colonies on the original plate which give rise to tramlines on the replica plate are thereby identified. Such a colony is transferred with a needle on to a plate of the minimal medium (MM) and cultured to provide a quantity of the particular *S. lividans* strain containing a plasmid of the present invention.

Using this procedure the *S. lividans* strains NCIB 11417, 11499 and 11500 were isolated.

(B) Procedure involving crossing (1) A cross is made by mixing together spores of the *S. lividans* strain NCIB 11499, which contains the plasmid SLP1.2, and spores of the *S. coelicolor* strain NCIB 11414 on a slant of the complete medium described by Hopwood, ibid (CM) and growing the mixture of spores thereon. The spores are harvested and plated on R2 medium plates containing histidine and uracil (for growth of *S. coelicolor*) and streptomycin (for inhibition of *S. lividans*), and spread with a lawn of spores of the *S. coelicolor* strain NCIB 11414. Growth on these plates gives some pocks which are picked with a needle as described in (A) and streaked out on a plate of the minimal medium (MM) containing histidine, uracil and streptomycin to give single isolated colonies. These are grown up and then replica plated on to a plate of R2 medium containing histidine, uracil and streptomycin, and spread with a lawn of spores of the strain NCIB 11414. Colonies on the original plate which give rise to tramlines on the replica plate are thereby identified. Such a colony is transferred with a needle on to a plate of the minimal medium containing histidine, uracil and streptomycin and cultured to provide a quantity of the particular *S. coelicolor* strain showing the lethal zygosis phenomenon.

Using this procedure the *S. coelicolor* strain having the John Innes reference number M200 was isolated; it did not prove possible to separate plasmid DNA from this strain.

(2) A cross is made by mixing together spores of the S. coelicolor strain M200 showing the lethal zygosis phenomenon with spores of the S. lividans strain NCIB 11416 on a slant of the complete medium (CM) and growing the mixture of spores thereon. The spores are harvested by plating on R2 medium plates containing no histidine or uracil (for inhibition of S. coelicolor) and no streptomycin (for growth of S. lividans), and spread with a lawn of spores of the strain NCIB 11416. Growth on these plates gives rise to some pocks which are treated as described under (1) above but with the omission from the media of histidine, uracil and streptomycin. This procedure yields particular S. lividans strains containing a plasmid of the present invention.

Using this procedure for the crossing of the S. coelicolor strain of reference number M200 with the S. lividans strain NCIB 11416 the S. lividans strains NCIB 11502 and 11503 were isolated.

Using an analogous procedure the S. lividans strain NCIB 11417 which contains the plasmid SLP1.1 was crossed with the S. coelicolor strain NCIB 11414 to give the S. coelicolor strain having the John Innes reference number M171, which was in turn crossed with the S. lividans strain NCIB 11416 leading to the isolation of the S. lividans strain NCIB 11501.

ISOLATION OF PLASMID (All percentages quoted are weight/volume.)

500 ml of a liquid medium containing 0.3% Difco Bacto yeast extract, 0.5% Difco Bacto peptone, 0.3% Oxoid malt extract, 1% glucose, 34% sucrose and 0.1% magnesium chloride is inoculated with 1 ml of a dense spore suspension of the micro-organism and this is grown at 30° C. with constant gyratory shaking for 44 hours. The mycelium is harvested by centrifugation for 30 minutes at 10,000 rpm in a Beckman JA14 rotor at 20° C.

The mycelium is washed in 10% w/v glycerol, resuspended in 50 ml of 0.01M Tris-HCl and 0.001M EDTA buffer of ph 8.0 (TE buffer) containing 34% sucrose, and maintained at 30° C. 10 ml of 0.25M EDTA (ethylene diamine tetra-acetic acid, Na salt), pH 8.0 is added followed by 5 ml lysozyme (50 mg/ml in 0.01M Tris). The mixture is incubated at 30° C. for 15 minutes, placed in an ice bath and treated with 50 ml of TE buffer containing 34% sucrose, 30 ml of 0.25M EDTA and 5 ml of 0.01M Tris (each of these being ice cold). Sodium dodecyl sulphate (SDS) dissolved in TE buffer is added to give a final concentration of 1% followed by sodium chloride to a final concentration of 1M. The lysis mixture is allowed to stand in ice for 2 hours or overnight and the chromosomal DNA/SDS precipitate is removed by centrifugation at 16,000 rpm and 4° C. for 1 hour in a Beckman JA20 rotor. Polyethylene glycol 6000 (PEG) is then added to the supernatant to give a final concentration of 10% and the mixture left for 2 hours or overnight at 4° C.

The flocculent DNA-PEG precipitate is harvested by centrifugation at 4,000 rpm for 4 minutes at 4° C. in a Beckman JA14 rotor and then redissolved in the minimum volume of 0.03M Tris, 0.005M EDTA and 0.05M NaCl buffer of pH 8.0 (TES buffer) (ca 8 ml). Ethidium bromide is added to a final concentration of 500 μg/ml and caesium chloride to a refractive index of 1.3925 (density 1.63 g/cc). The gradients are centrifuged in a Beckman 40 rotor at 36,000 rpm and 20° C. for 60 hours in a Beckman L2-65B centrifuge. The plasmid DNA is removed from the gradient by the careful insertion of a 1 ml syringe. Ethidium bromide is removed from the plasmid DNA by extracting three times with two volumes of ice-cold isoamyl alcohol. Caesium chloride is removed by dialysis against three changes of 1000 volumes TE buffer at 4° C. for 6 hours. The yield of DNA is typically from 10 to 30 μg depending on the strain.

Using the procedure described above the six micro-organisms NCIB 11417, 11499, 11500, 11501, 11502 and 11503 yielded respectively the plasmids SLP1.1, SLP1.2, SLP1.3, SLP1.4, SLP1.5 and SLP1.6. The cleavage sites of the plasmid DNA were studied in the usual manner for the restriction endonucleases EcoRI(E), HindIII (H), SalGI (G), BamHI (B), and SalPI or PstI (P). The plasmids were found to contain a common segment of DNA of estimated molecular weight $6.25 \times 10^6$ daltons or 6.25 megadaltons containing one site for cleavage by EcoRI, two sites for cleavage by HindIII and two sites for cleavage by SalGI. All of the plasmids with the exception of SLP1.6 were found to contain an additional segment containing from one to five cleavage sites. The cleavage sites in the SLP1.6 plasmid are shown in the accompanying Figure together with the estimated distances between them in megadaltons. The additional segment in the other five plasmids is in each case inserted into the portion of the SLP1.6 plasmid which is represented by a thickened line. Details of these segments are given in the following Table 2. The estimated sizes were obtained by comparison of the cleavage fragments obtained with standard cleavage fragments obtained from bacteriophage lambda as measured at Stanford University, Calif., U.S.A. using agarose gel electrophoresis.

TABLE 2

| Plasmid | Estimated Size Md | Restriction Sites | | | | | Extra Segment (1) |
|---|---|---|---|---|---|---|---|
| | | E | H | G | B | P | |
| SLP1.6 | 6.25 | 1 | 2 | 2 | 0 | 0 | None |
| SLP1.4 | 6.4 | 1 | 3 | 2 | 0 | 0 | H |
| SLP1.3 | 6.88 | 1 | 3 | 3 | 0 | 0 | H G |
| SLP1.1 | 7.13 | 1 | 3 | 3 | 0 | 1 | H G P |
| SLP1.5 | 7.28 | 1 | 3 | 3 | 0 | 1 | H G P |
| SLP1.2 | 8.23 | 1 | 3 | 3 | 1 | 2 | H G P P B |

(1)Inserted from left hand to right hand end in clockwise fashion into portion of SLP1.6 shown as thickened line in the Figure.

EXAMPLE 2: TRANSFORMATION OF A STREPTOMYCES WITH AN SLP PLASMID (a) Transformation Procedure 0.2 ml of a suspension of approximately $10^7$ protoplasts (prepared from the S. lividans strain NCIB 11416 by the method of Hopwood et al, Nature, 1977, 268, 171 but using 1 mg/ml of lysozyme alone rather than a mixture of lysozyme and Lytic Enzyme No. 2) in medium P (Hopwood and Wright, Molecular and General Genetics, 1978, 162, 307) is centrifuged for 7 minutes. After pelleting the protoplasts, the supernatant is discarded and the protoplasts resuspended in the small volume of remaining medium P by gently tapping the bottom of the tube with a finger. Approximately 2 μg of SLP DNA (ca $7 \times 10^{10}$ molecules—prepared from an SLP+ strain as described in Example 1) in a small volume of medium P are added to the protoplasts and the tube slowly rotated to ensure thorough mixing. 0.5 ml of a solution of 20%(w/v) polyethylene glycol (PEG) 1000 in P medium is added and efficient mixing of the protoplasts and PEG achieved by drawing the total volume up and down a Pasteur pipette twice. After 1 minute, 4 ml of medium P are added and the protoplasts are pelleted by centrifugation at 1000 g for 7 minutes. The supernatant is discarded and the protoplasts again resuspended in the small volume of remaining liquid by gently tapping the tube with a finger. 0.2 ml of medium P is then added and serial dilutions of the mixture are made by taking 20 μl and diluting successively into 0.18 ml of medium P down to a $10^{-5}$ dilution. Using a 1 ml pipette, each of the successive dilutions is transferred to plates of R2 medium (Hopwood and Wright, ibid), the protoplasts being spread gently over the surface of the plates with a wire loop or glass spreader. Regeneration of the protoplasts and subsequent growth to produce mature sporulating confluent lawns or, in the case of the more dilute samples, single colonies, is allowed to occur for a period of 7 to 10 days at 30° C.

(b) Detection of Transformation

To assay for transformation even at low frequencies, the regeneration plates containing confluent lawns of regenerated protoplasts are taken and the spores harvested from each as follows. 10 ml of sterile distilled water is added to the plate and the surface of the culture gently scraped with a wire loop to remove the spores. The liquid is then transferred to a small bottle and shaken vigorously to break up the spore chains into single spore units. The preparation is then filtered through cotton wool to remove mycelial debris and the resulting spore suspension concentrated by centrifugation at 1000 g for 15 minutes. The supernatant is discarded and the remaining spore pellet resuspended in 0.3 ml of 20% v/v glycerol. Serial dilutions of the preparation are made down to $10^{-5}$ by successive transfer of 0.1 ml of the spore suspension to 0.9 ml of 20% v/v glycerol. The spores can then be stored at −20° C. with little loss of viability. 0.1 ml aliquots of some of the dilution series (e.g. $10°$, $10^{-2}$, $10^{-4}$) of each of the harvested plates are then transferred to R2 medium plates which have also received sufficient spores of the NCIB 11416 strain originally used in the transformation procedure to produce a confluent lawn. Transformants can typically be detected after 3 days' growth at 30° C. by the appearance of "pocks" resulting from "lethal zygosis" expressed by spores containing the plasmid in expressible form within the lawn.

(c) Recovery of Transformants

The transformants are recovered by picking spores from the centre of the "pock" using a fine wire needle to an agar plate of minimal medium (Hopwood, Bacteriological Reviews, 1967, 31, 373).

Varying levels of transformation have been observed in experiments with the plasmids SLP1.1, SLP1.2, SLP1.3, SLP1.4, SLP1.5 and SLP1.6, ranging from at least above 1% for SLP1.3 to SLP1.6, through typical figures of 18, 10, 23, 17 and 15% for SLP1.1 to as high as 85% for SLP1.2 (the percentages referring to that proportion of the recipient protoplasts containing at least one plasmid per protoplast).

We claim:

1. A Streptomyces plasmid which has the characteristic that it comprises that portion of the DNA sequence of the plasmid, designated SLP 1.6 and shown in the Figure, required for the expression of replication and that its presence in non-integrated form in a microorganism of the species *Streptomyces lividans* confers on that microorganism the properties (a) of forming "pocks" when grown on a "lawn" of that strain of microorganism deposited with the NCIB under the reference number 11416, and (b) of not forming "pocks" when grown on a "lawn" of that strain of microorganism deposited with the NCIB under the reference number 11417, said plasmid being in isolated form.

2. A Streptomyces plasmid selected from the group consisting of the plasmids isolable, respectively, from the strains of microorganism deposited with the NCIB under the reference numbers 11417, 11499, 11500, 11501, 11502, and 11503, said plasmid having the structural features given in the following Table

| Plasmid | Estimated Size Md | Restriction Sites for the Endonucleases E, H, G, B, P | | | | | Extra Segment (Inserted from left hand to right hand end in clockwise fashion into portion of SLP 1.6 shown as thickened line in the FIG.) |
| --- | --- | --- | --- | --- | --- | --- | --- |
| | | E | H | G | B | P | |
| SLP 1.6 | 6.25 | 1 | 2 | 2 | 0 | 0 | None |
| SLP 1.4 | 6.4 | 1 | 3 | 2 | 0 | 0 | H |
| SLP 1.3 | 6.88 | 1 | 3 | 3 | 0 | 0 | H G |
| SLP 1.1 | 7.13 | 1 | 3 | 3 | 0 | 1 | H G P |
| SLP 1.5 | 7.28 | 1 | 3 | 3 | 0 | 1 | H G P |
| SLP 1.2 | 8.23 | 1 | 3 | 3 | 1 | 2 | H G P P B | and being in isolated form.

3. A Streptomyces plasmid which comprises that portion of the DNA sequence of the plasmid, designated SLP 1.6 and shown in the Figure, required for the expression of replication and lethal zygosis, said plasmid being in isolated form.

4. A biologically pure culture of a microorganism containing a plasmid as defined in claim 1, 2 or 3 in non-integrated form, wherein the microorganism is of the species *Streptomyces lividans*.

5. A biologically pure culture of a microorganism of the species *Streptomyces lividans* characterized by the properties (a) of forming "pocks" when grown on a "lawn" of that strain of microorganism deposited with the NCIB under the reference member 11416, and (b) of not forming "pocks" when grown on a "lawn" of that strain of microorganism deposited with the NCIB under the reference number 11417.

6. A biologically pure culture of a strain of *Streptomyces lividans* selected from the group consisting of those strains deposited with the NCIB under the reference numbers 11417, 11499, 11500, 11501, 11502 and 11503.

* * * * *